United States Patent
Izmirli et al.

(10) Patent No.: US 11,950,932 B2
(45) Date of Patent: Apr. 9, 2024

(54) MECHANICAL DESIGN CONSIDERATIONS FOR TABLE-MOUNTED DEVICE USED AS A SUB-ASSEMBLY IN A MAGNETIC TRACKING SYSTEM WORKING IN CONJUNCTION WITH AN X-RAY IMAGING SYSTEM

(71) Applicant: St. Jude Medical International Holding S.à r.l., Luxembourg (LU)

(72) Inventors: Alon Izmirli, Ganot Hadar (IL); Guy Hevel, Zikron Yaakov (IL); Adrian Herscovici, Or Akiva (IL); Yuval Vaknin, Hanaton (IL); David Jacobs, Nahariya (IL)

(73) Assignee: ST JUDE MEDICAL INTERNATIONAL HOLDING, SA.R.L., Luxembourg (LU)

( * ) Notice: Subject to any disclaimer, the term of this patent is extended or adjusted under 35 U.S.C. 154(b) by 879 days.

(21) Appl. No.: 16/969,089

(22) PCT Filed: Feb. 9, 2019

(86) PCT No.: PCT/EP2019/053217
§ 371 (c)(1),
(2) Date: Aug. 11, 2020

(87) PCT Pub. No.: WO2019/155036
PCT Pub. Date: Aug. 15, 2019

(65) Prior Publication Data
US 2021/0030365 A1    Feb. 4, 2021

Related U.S. Application Data

(60) Provisional application No. 62/783,047, filed on Dec. 20, 2018, provisional application No. 62/629,086, filed on Feb. 11, 2018.

(51) Int. Cl.
A61B 5/05    (2021.01)
A61B 5/00    (2006.01)
(Continued)

(52) U.S. Cl.
CPC ............ *A61B 5/704* (2013.01); *A61B 5/0033* (2013.01); *A61B 5/05* (2013.01); *A61B 5/706* (2013.01);
(Continued)

(58) Field of Classification Search
CPC ......... A61B 5/704; A61B 5/0033; A61B 5/05; A61B 5/706; A61B 2090/2046; A61B 2090/3966; A61B 2090/3954
See application file for complete search history.

(56) References Cited

U.S. PATENT DOCUMENTS 6,484,049 B1    11/2002    Seeley et al.
2003/0013340 A1*    1/2003    Martin ............... G01R 1/06738
439/488

(Continued)

FOREIGN PATENT DOCUMENTS

DE    102010011589 A1    9/2011
WO    2018/109555 A2    6/2018

OTHER PUBLICATIONS

U.S. Appl. No. 62/663,871, filed Apr. 27, 2018, St. Jude Medical International Holding S.á r.l.

*Primary Examiner* — Joel F Brutus
(74) *Attorney, Agent, or Firm* — Billion & Armitage

(57) ABSTRACT

A registration fixture is configured for use with a medical imaging system. The registration fixture comprises a rigid internal structure comprising a plurality of fiducial markers arranged in a predefined pattern. The registration fixture
(Continued)

further comprises a housing configured to surround the rigid internal structure. The registration fixture is configured to be mounted on a patient table.

22 Claims, 9 Drawing Sheets

(51) Int. Cl.
*A61B 34/20* (2016.01)
*A61B 90/00* (2016.01)

(52) U.S. Cl.
CPC .............. *A61B 34/20* (2016.02); *A61B 90/39* (2016.02); *A61B 2034/2046* (2016.02); *A61B 2090/3954* (2016.02); *A61B 2090/3966* (2016.02)

(56) References Cited

U.S. PATENT DOCUMENTS

| | | |
|---|---|---|
| 2009/0213997 A1 | 8/2009 | Maschke |
| 2014/0114173 A1* | 4/2014 | Bar-Tal .................... A61B 6/54 600/409 |
| 2014/0121497 A1 | 5/2014 | Coppens et al. |
| 2015/0157405 A1* | 6/2015 | Beeckler ............ A61B 18/1492 606/13 |
| 2015/0247944 A1* | 9/2015 | Govari .................. A61B 5/062 324/318 |
| 2016/0184041 A1* | 6/2016 | Gafford ................ A61B 18/148 606/174 |
| 2016/0287133 A1 | 10/2016 | Eichler et al. |

* cited by examiner

MECHANICAL DESIGN CONSIDERATIONS FOR TABLE-MOUNTED DEVICE USED AS A SUB-ASSEMBLY IN A MAGNETIC TRACKING SYSTEM WORKING IN CONJUNCTION WITH AN X-RAY IMAGING SYSTEM

CROSS-REFERENCE TO RELATED APPLICATIONS

This International patent application claims priority to U.S. provisional patent application No. 62/629,086, filed 11 Feb. 2018 (the '086 application); and this International patent application claims priority to U.S. provisional patent application No. 62/783,047, filed 20 Dec. 2018 (the '047 application). The '086 application and the '047 application are both hereby incorporated by reference as though fully set forth herein.

BACKGROUND a. Field

The present disclosure relates to an apparatus configured to be placed in the path of an X-ray and in the vicinity of a magnetic field. This apparatus may include optical-magnetic registration plate, including a predefined pattern of fiducial elements, which can be used to register 2D X-ray images within a 3D coordinate system.

b. Background

A wide variety of medical devices may be inserted into the body to diagnose and treat various medical conditions. Catheters, for example, are used to perform a variety of tasks within human bodies and other bodies, including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface of the heart.

Catheters are typically routed to a region of interest through the body's vascular system. In a conventional catheterization, a micro-puncture needle (e.g., a Seldinger needle) is used to puncture the skin surface to gain access to, for example, a femoral artery, and a guide wire is then inserted through the needle before the needle is removed. A catheter sheath with a dilator inserted in it is then inserted over the guide wire. The dilator and the guide wire are then removed, leaving the sheath in place in the femoral artery. The sheath has an inner diameter greater than the outer diameter of a catheter to be used in the procedure. The catheter is then inserted into the sheath, and the sheath and/or catheter are subsequently threaded through the vasculature to a region of interest. Typically, but not necessarily, the catheter is then moved longitudinally relative to the sheath so as to extend from the distal end of the sheath to the region of interest. The longitudinal movement may be done either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the positions of medical devices within the body. These systems typically rely on the generation of electrical or magnetic fields and the detection of induced voltages and currents on position sensors attached to the medical device and/or external to the body. The information derived from these systems is then provided to a physician through, for example, a visual display. Oftentimes, a representation of the medical device is displayed relative to a computer model or one or more images (including, but not limited to, fluoroscopic images) of the anatomical region in which the device is being maneuvered. To display the medical device at the correct location relative to the model or image, the model or image is registered within the coordinate system of the navigation system. This can be accomplished by having a set of fiducial markers that can be detected on the image or model and also be associated with known locations within the navigation system. The foregoing discussion is intended only to illustrate the present field and should not be taken as a disavowal of claim scope.

BRIEF SUMMARY OF THE DISCLOSURE

A registration fixture configured for use with a medical imaging system is disclosed. The registration fixture comprises a rigid internal structure comprising a plurality of fiducial markers arranged in a predefined pattern. The registration fixture further comprises a housing configured to surround the rigid internal structure. The registration fixture is configured to be mounted on a patient table.

In an embodiment, a registration fixture configured for use with a medical imaging system comprises: a rigid internal structure comprising a plurality of fiducial markers arranged in a predefined pattern; a housing configured to surround the rigid internal structure; and a floating mechanism configured to allow the rigid internal structure to float within the housing; wherein the fixture is configured to be mounted on a patient table.

In another embodiment, a registration fixture configured for use with a medical imaging system comprises: a rigid internal structure comprising a plurality of fiducial markers arranged in a predefined pattern; and a housing configured to surround the rigid internal structure; wherein the fixture is configured to be mounted on a patient table; and wherein the internal rigid structure comprises a stack of unidirectional carbon fiber layers.

The foregoing and other aspects, features, details, utilities, and advantages of the present disclosure will be apparent from reading the following description and claims, and from reviewing the accompanying drawings.

DETAILED DESCRIPTION

Figure 1:
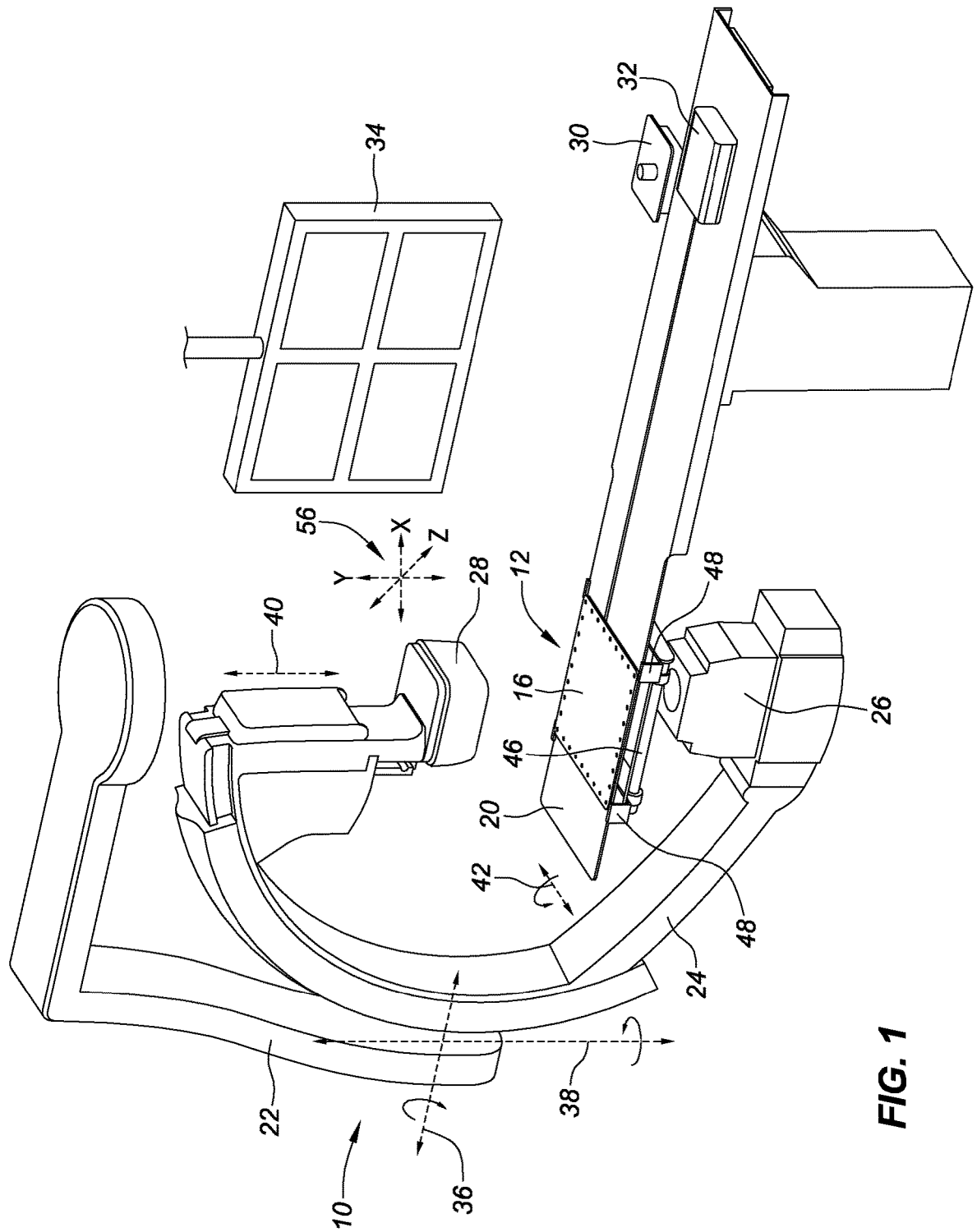
FIG. 1 is a diagrammatic view of an electrophysiology lab including an imaging system and a localization system, in accordance with an embodiment of the present teachings.
Figure 2A:
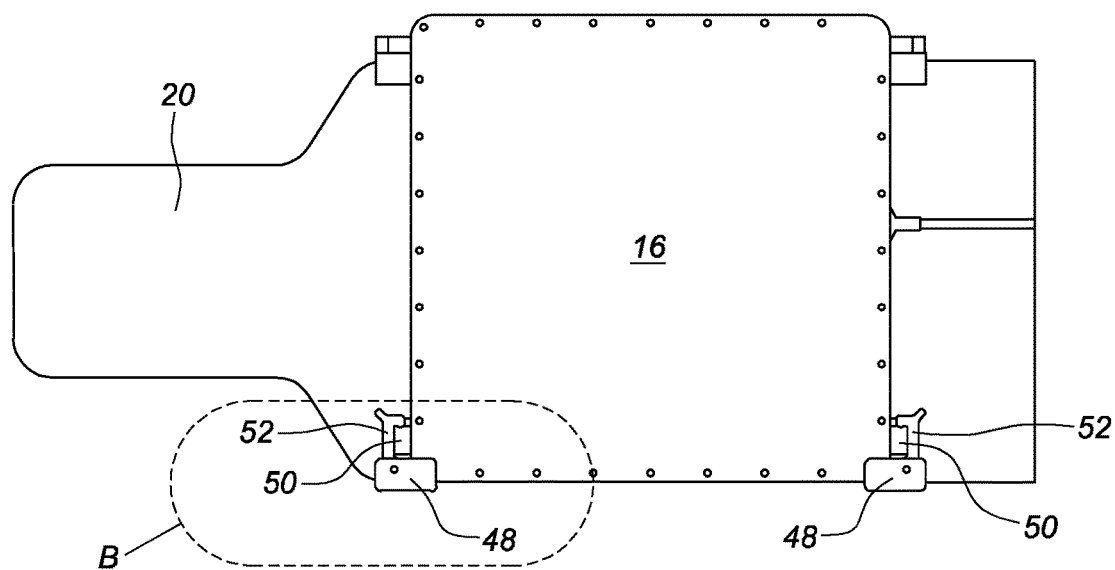
FIG. 2A is a top view of an example of a registration plate and means for attaching it to a magnetic transmitter and/or patient table.
Figure 2B:
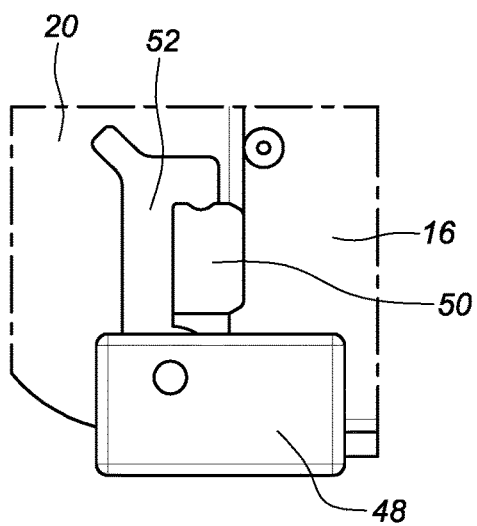
FIG. 2B is an enlarged view of section B from FIG. 2A, showing the transmitter clamp bracket in a closed configuration.
Figure 2C:
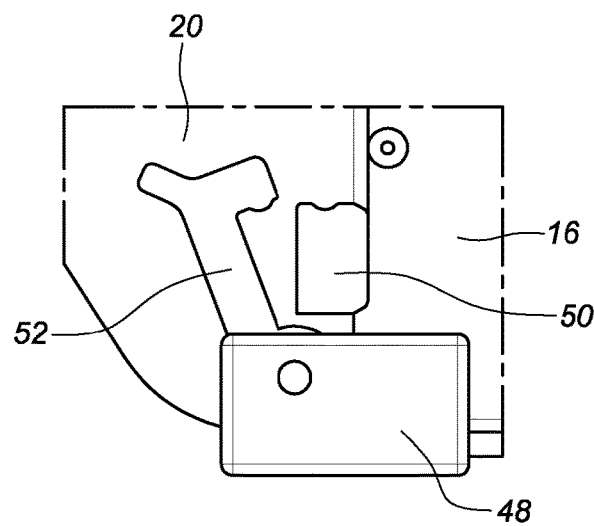
FIG. 2C is an enlarged view of section B of FIG. 2A, showing the transmitter clamp bracket in an open configuration.
Figure 3A:
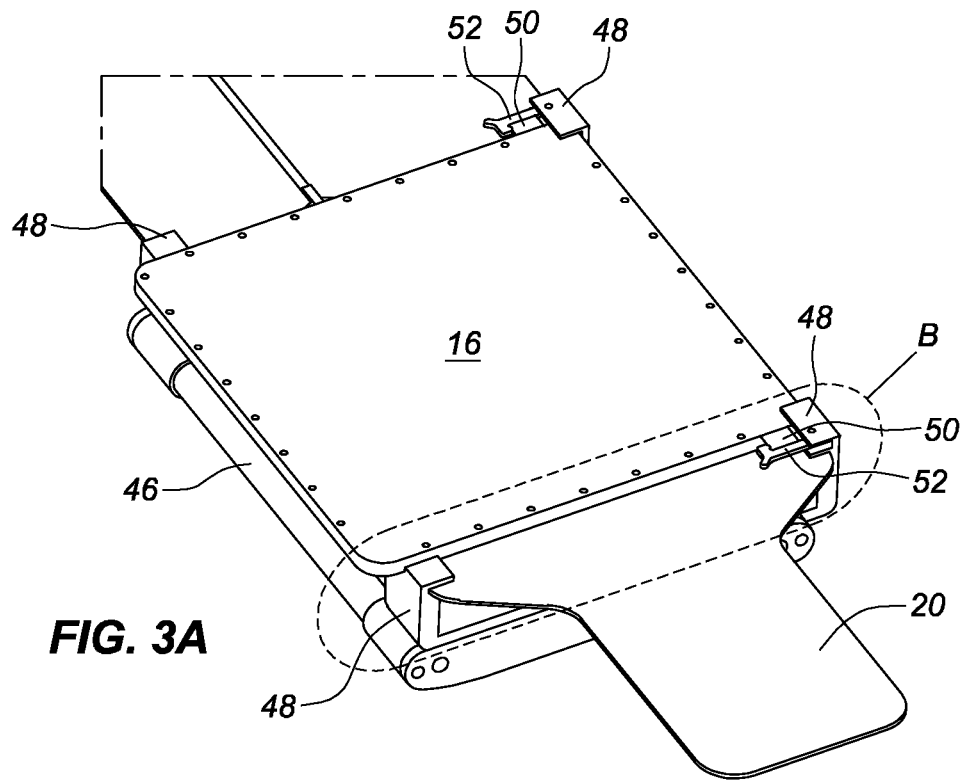
FIG. 3A is an isometric view of portions of the localization system.
Figure 3B:
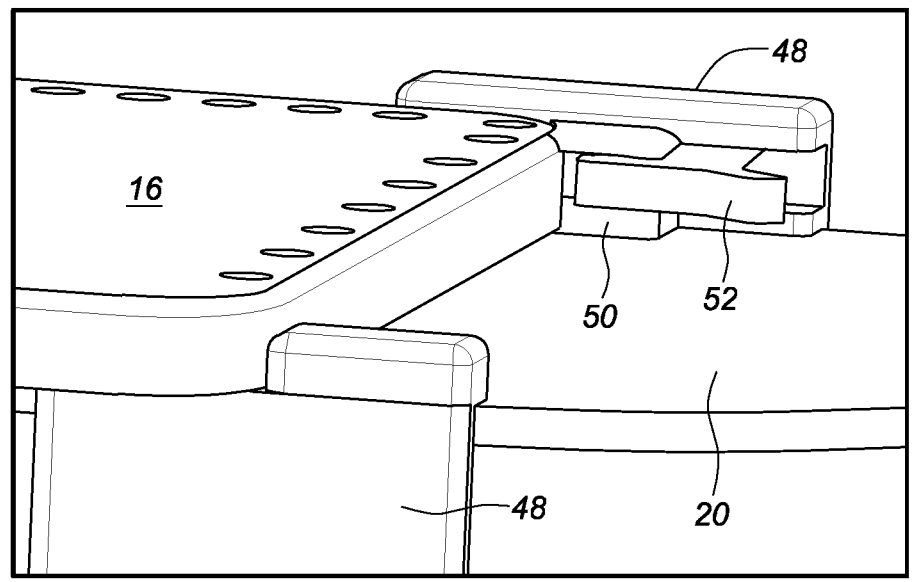
FIG. 3B is an enlarged side-angle view of section B of FIG. 3A.

Referring to the drawings wherein like reference numerals are used to identify identical components in the various views, FIG. 1 illustrates an electrophysiology lab including an imaging system 10 (e.g., a fluoroscopic or other imaging system) and a localization system 12. The localization system 12 may comprise and an optical-magnetic registration system (also referred to as "magnetic tracking system") for calculating the geometric relationship between the actual locations of fiducial markers 15 (e.g., radio-opaque ball or line elements) on or within a fiducial plate or layer 14 (see FIG. 4) within an optical-magnetic registration fixture or plate 16 (also referred to as "omni-magnetic registration plate," "omni-magnetic registration fixture," "OMRP plate," "OMRP fixture," "plate," or "fixture") and the detected positions of the fiducial markers 15 within an image generated by the imaging system 10. When a patient's body (not shown for clarity) is positioned on a table 20 (e.g., a patient table, a platform bed, a gurney, or a similar patient support) within the electrophysiology lab, a region of interest, such as the patient's heart (not shown for clarity), may overlay the OMRP plate 16, such that images of the patient's heart include images of the fiducial markers 15 within the fiducial layer 14. This allows for registration of the coordinate system of the imaging system 10 with the coordinate system of the localization system 12 based on known locations of the fiducial markers 15 in each of the coordinate systems. Registration of the two coordinate systems further allows for real-time localization of a medical device—such as an electrophysiological (EP) mapping catheter, an intracardiac echocardiography (ICE) catheter, or an ablation catheter, for example—within the patient's heart (or other region of interest) based on images including the fiducial markers 15.

The imaging system 10 is provided to acquire images of the heart or other anatomical regions of interest and comprises a fluoroscopic imaging system in the illustrated embodiment. The imaging system 10 has a structure that is movable relative to the various components of the localization system 12 and relative to the patient's body and to the table 20 supporting the body. The imaging system 10 may include a number of structural components including, in the illustrated embodiment, a support 22, an arm 24, a radiation emitter 26, and a radiation detector 28. The imaging system 10 may also include an electronic control unit 30 for controlling operation of the system 10, a processing unit 32 for calculating geometry parameters of the systems 10 and 12, and output devices such as a display 34.

The support 22 provides a means for supporting and moving the arm 24, the emitter 26, and the detector 28 relative to the OMRP plate 16 (and relative to a patient's body overlaying the OMRP plate 16). The support 22 may be connected to the arm 24 (as shown). In other embodiments, the support 22 may be suspended from a ceiling in the EP lab or affixed to rails (not shown) or similar structures. The support may be moved by mechanical, electrical, or electromechanical devices (not shown). The support 22 may be configured to rotate with the arm 24, the emitter 26, and the detector 28 about an axis 36 to position the arm 24, the emitter 26, and the detector 28 relative to the OMRP plate 16.

The arm 24 provides a means for supporting the emitter 26 and the detector 28 relative to the OMRP plate 16. The arm 24 may be substantially C-shaped (i.e., a "C-arm") to provide sufficient clearance relative to a patient's body and the table 20. The arm 24 is configured to rotate in either direction about an axis 38 relative to the support 22 to cause corresponding movement of the emitter 26 and the detector 28, as well as to position the emitter 26 and the detector 28 relative to the OMRP plate 16 to permit images to be acquired from a variety of angles or orientations.

The emitter 26 is provided to emit electromagnetic radiation (e.g., x-rays) over a field of view between the emitter 26 and the detector 28, including the OMRP plate 16 and an overlying anatomical region of interest in a patient's body. The emitter 26 is disposed at one end of the arm 24. In an embodiment, the emitter 26 may be activated by a control pedal (not shown) operated by a physician, for example.

The detector 28 captures electromagnetic radiation passing through the plate 16 and anatomical region of interest in a patient's body and generates signals used to create images of the OMRP plate 16 and the region of interest. In one embodiment, the detector 28 may comprise a flat detector and may be configured to rotate about the axis 36 relative to the arm 24. The detector 28 may also be movable relative to the arm 24 along an axis 40 to vary the distance between the emitter 26 and the detector 28 (i.e., the "source to image" distance or "SID"). The detector 28 is disposed at an opposite end of the arm 24 relative to the emitter 26.

The relative movement of the imaging system 10 and other objects within the electrophysiology lab create various degrees of freedom that the localization system 12 may need to account for. The arm 24 rotates about axes 36, 38, and 42, and moves along axis 40. The table 20 may move relative to the imaging system 10 (or vice versa) in either direction along three orthogonal axes resulting in as many as seven degrees of freedom.

A display 34 is provided to convey information to a physician to assist in diagnosis and treatment. The display 34 may comprise one or more computer monitors or other display devices. The display 34 may present fluoroscopy images and a graphical user interface (GUI) to the physician. The GUI may communicate a variety of information including, for example, a fluoroscopic image of an anatomical region of interest, such as a heart, along with any fiducial markers 15 within the fiducial layer 14 of the OMRP plate 16 underlying the anatomical region of interest. Image data to the display 34 may be captured and processed by the processing unit 32, such that a 3D matrix of the fiducial markers 15 is accurately projected onto the 2D fluoroscopic image seen on the display 34. The GUI may also communicate information regarding the anatomy of a patient's heart, electrophysiology data associated with the heart, as well as images and positional information for one or more therapeutic or diagnostic medical devices being used in or around the patient's heart.

In accordance with one embodiment of the present teachings, the localization system 12 is used for associating fiducial markers 15 detected on a fluoroscopic image to their "real-world" positions on the OMRP plate 16. The localization system 12 may also be used to determine the position of the imaging system 10 within coordinate system 56 and, in particular, various components of imaging system 10. The system 12 employs magnetic fields and may comprise the system made available under the trademark MediGuide™ by St. Jude Medical, Inc. and generally shown and described in, for example, commonly owned U.S. Pat. No. 7,386,339, the entire disclosure of which is incorporated herein by reference.

The system 12 may include magnetic field transmitters 46, which can be associated with (e.g., releasably fixed to) the OMRP plate 16 or located within the OMRP plate 16. In the embodiment shown in FIG. 1, the magnetic field transmitters 46 are positioned at fixed locations (i.e., positions and orientations) with respect to the OMRP plate 16 via transmitter clamps 48, which may clamp onto the OMRP plate 16 via grooves (not shown) in the OMRP plate 16 and/or another means of attachment. As shown in FIGS. 2A-2C and 3A-3B, the OMRP plate 16 may include extensions 50 positioned at or near one or more of its four corners. Transmitter clamp brackets 52 can close around the extensions 50 to more securely hold the OMRP plate 16 in place with respect to the transmitters 46.

Magnetic field transmitters 46 generate magnetic fields that cause a response in magnetic sensors 54 (shown to better advantage in FIG. 5) indicative of the location and orientation of the magnetic sensors 54 within the magnetic fields and within coordinate system 56. In an embodiment, the magnetic sensors 54 may be located at or near the periphery of the OMRP plate 16 so as to limit potential interference with the X-ray field of view. Additional magnetic field sensors (not shown) may be located within a medical device, on a patient, or at other locations within coordinate system 56.

The OMRP plate 16 and its associated sub-assembly components will now be described in further detail with respect to FIGS. 4-10.

As discussed above, catheterization procedures in various medical applications require accurate real-time localization of the catheter tip in the human body. One of the main methods employed for localization is X-ray imaging. An alternative method is to use magnetic localization projected on previously acquired X-ray images. The advantage of this method is a significant reduction of the X-ray exposure for the patient and medical staff.

The following sub-assemblies are the main components of a magnetic tracking system, such as the above-described localization system 12: a magnetic field generator (e.g., magnetic field transmitters 46), an optic-magnetic registration method, a control unit 30, a processing unit 32, and sensor-enabled tools (e.g., EP mapping catheters, ICE catheters, or ablation catheters). The region of interest for the magnetic tracking may overlap the X-ray field of view, and therefore, in some configurations, the magnetic field transmitters 46 and the optic-magnetic registration device (e.g., OMRP plate 16) can affect the performance of the X-ray imaging system 10. One of the options for minimal integration of the magnetic tracking system with the X-ray imaging system 10 includes placement of the magnetic field transmitter 46 and the OMRP plate 16 on the patient table-top, as can be seen in FIG. 1.

The generation of a well-defined electro-magnetic field, with the transmitters overlapping the X-ray field of view, is described in commonly owned U.S. Patent Application Publication Number US 2016/0287133 A1, the entire disclosures of which are incorporated herein by reference. The optic-magnetic registration can be achieved by placing an array of radio-opaque fiducials visible in the X-ray image, as described, for example, in commonly owned U.S. Patent Application No. 62/663,871, the entire disclosure of which is incorporated herein by reference. This invention can also be associated with commonly owned International Patent Application Number PCT/IB2017/001660 (Publication Number WO 2018/109555 A2), the entire disclosure of which is incorporated herein by reference, involving related housings or enclosures.

The present disclosure describes the major considerations for a magnetic tracking system table-mounted sub-component design working in conjunction with an X-ray imaging system. As shown, for example, in FIGS. 4 and 5, the OMRP plate 16 comprises a table-mounted device and its corresponding sub-assembly with or without the magnetic transmitters. The major design considerations, discussed below, allow for a robust table-mounted device with reduced impact on the performance of the X-ray imaging system 10.

As discussed further below, in an effort to reduce the impact of the sub-components of the localization system 12 on the performance of the X-ray imaging system 10, the following design considerations were taken into account: reduced X-ray attenuation, reduced X-ray image artifacts, reduced impact on X-ray system movement envelope, and minimal impact on patient comfort.

Reduced X-Ray Attenuation

Reduced impact on the X-ray radiation level can be achieved with a selection of materials with low X-ray attenuation and minimal thickness. The materials for such a design can include stacked carbon fiber layers and polymethacrylimide structural foam, similar to the design employed for X-ray system table-tops. These materials can form the OMRP plate 16, including the table-mounted sub-assembly with a protective housing 60 (including a top housing 60a and a bottom housing 60b), as shown in FIGS. 4-10.

Figure 4:
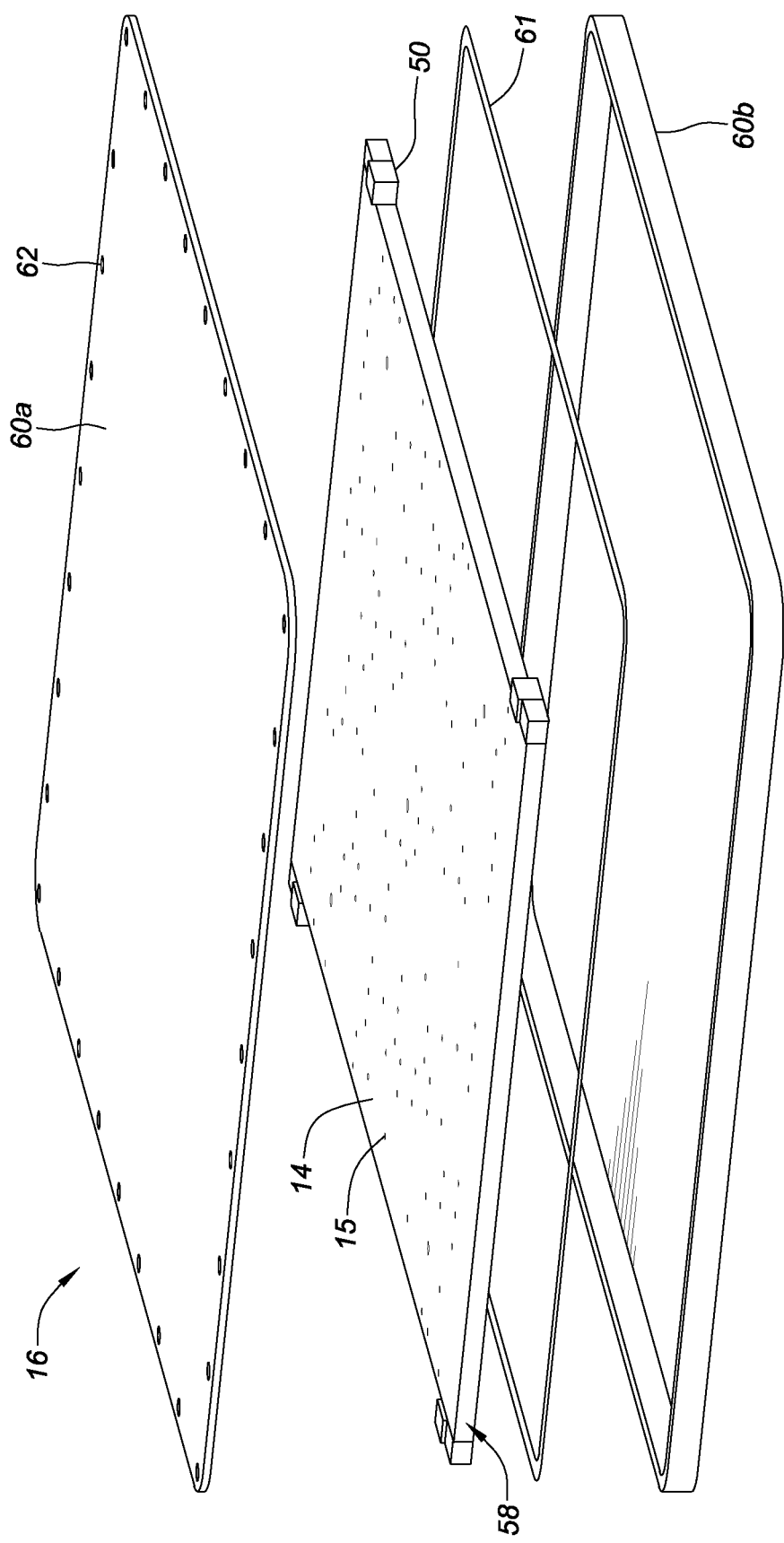
FIG. 4 is an exploded view of an example of a registration plate.

FIG. 4 illustrates further exemplary details of the OMRP plate 16 comprised of a rigid internal structure 58 including a fiducial layer 14 with fiducial markers 15 arranged in a pattern. As described above with respect to FIGS. 2A-2C and 3A-3B, tabs or extensions 50 may protrude at or near one or more of the four corners of the rigid internal structure 58 of the OMRP plate 16. These extensions 50 may be used to secure the rigid internal structure 58 in place within the protective housing 60 and/or with respect to other elements, such as the table 20 or the transmitters 46 (shown in FIGS. 1 and 3A). A silicon gasket 61 may be used to seal the OMRP plate 16 and protect the internal components of the rigid internal structure 58 from humidity. Through holes 62 for screws may be used to sandwich the rigid internal structure 58 of the OMRP plate 16 between the top housing 60a and the bottom housing 60b.

Figure 5:
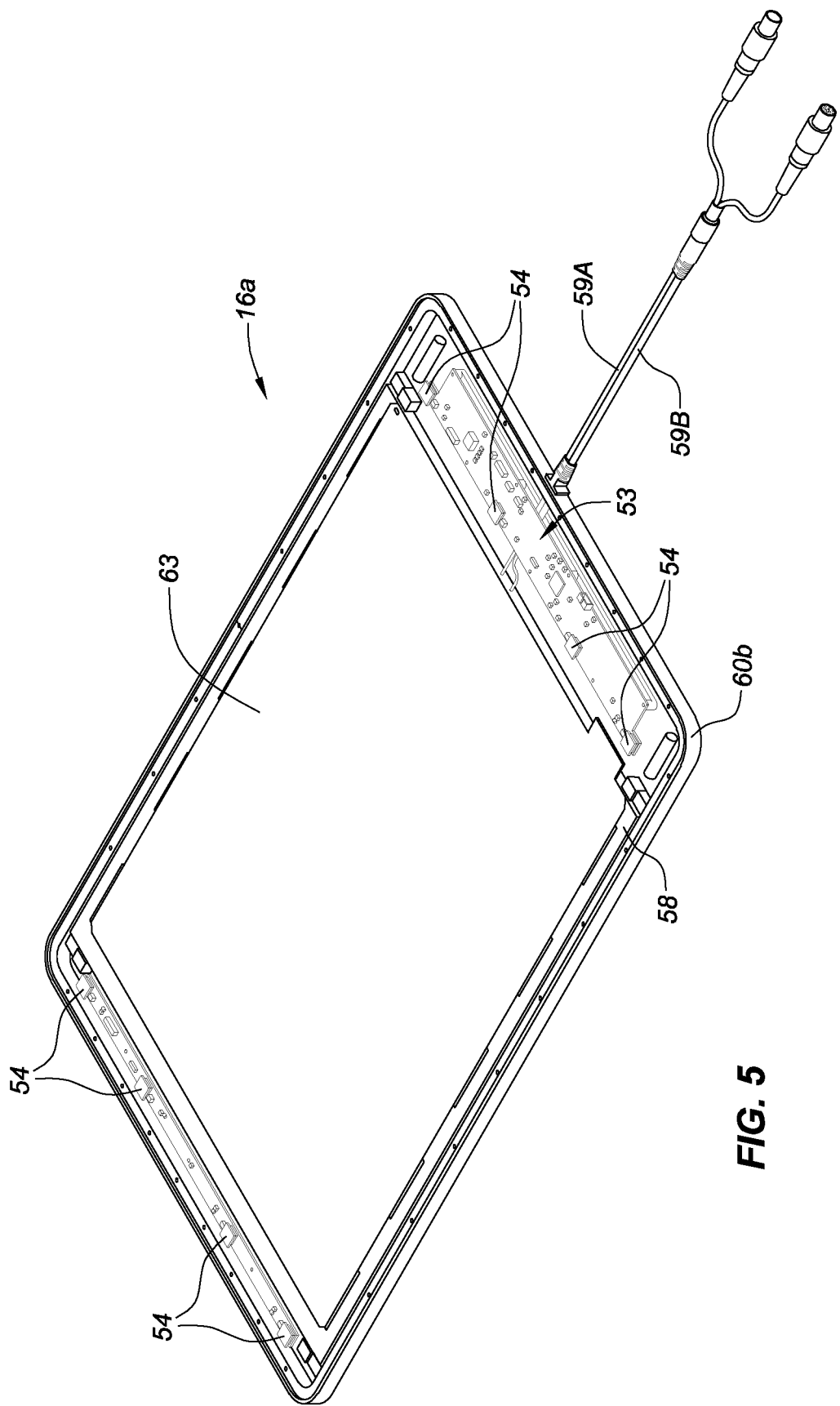
FIG. 5 is an isometric view of the registration plate with the top housing removed revealing various internal components.

Reduced X-ray attenuation can also be achieved by placing any X-ray visible elements 53, such as X-ray detection sensors, magnetic sensors 54, and electronics circuits, outside or at the periphery of the X-ray field of view. An example of positioning of non-transparent elements within the protective housing 60, with limited caudal-cranial angulation, is shown in FIG. 5. Interconnection wires, such as wires 59A and 59B, can be as thin as possible, and the routing should follow the sub-assembly edges. The interconnection wires 59A and 59B may extend from an internal portion of the OMRP plate 16a to the processing unit 32, the electronic control unit 30 and/or the display 34, for example. Aluminum may be preferable over copper for the composition of the interconnection wires 59A and 59B due to the respective X-ray transparency properties of aluminum and copper, including density and mass attenuation coefficient. In some embodiments, low attenuation internal flex cables may traverse the rigid internal structure.

In addition to the magnetic transmitter 46 (discussed above with respect to FIGS. 1 and 3A) located at the periphery of the OMRP plate and/or the X-ray field of view, other types of magnetic transmitters may be located within the X-ray field of view as long as they are minimally occlusive or nearly transparent to fluoroscopy. For example, a flat coil assembly 63 may comprise thin, flat PCB-type coils—such as those described in commonly owned US Patent Application Publication Number US 2016/0287133 A1 and in commonly owned International Patent Application Publication Number PCT/IB2017/001660 (Publication Number WO 2018/109555 A2)—can form one or more layers of the internal portion of the OMRP plate 16a, as shown in FIG. 5.

Figure 6:
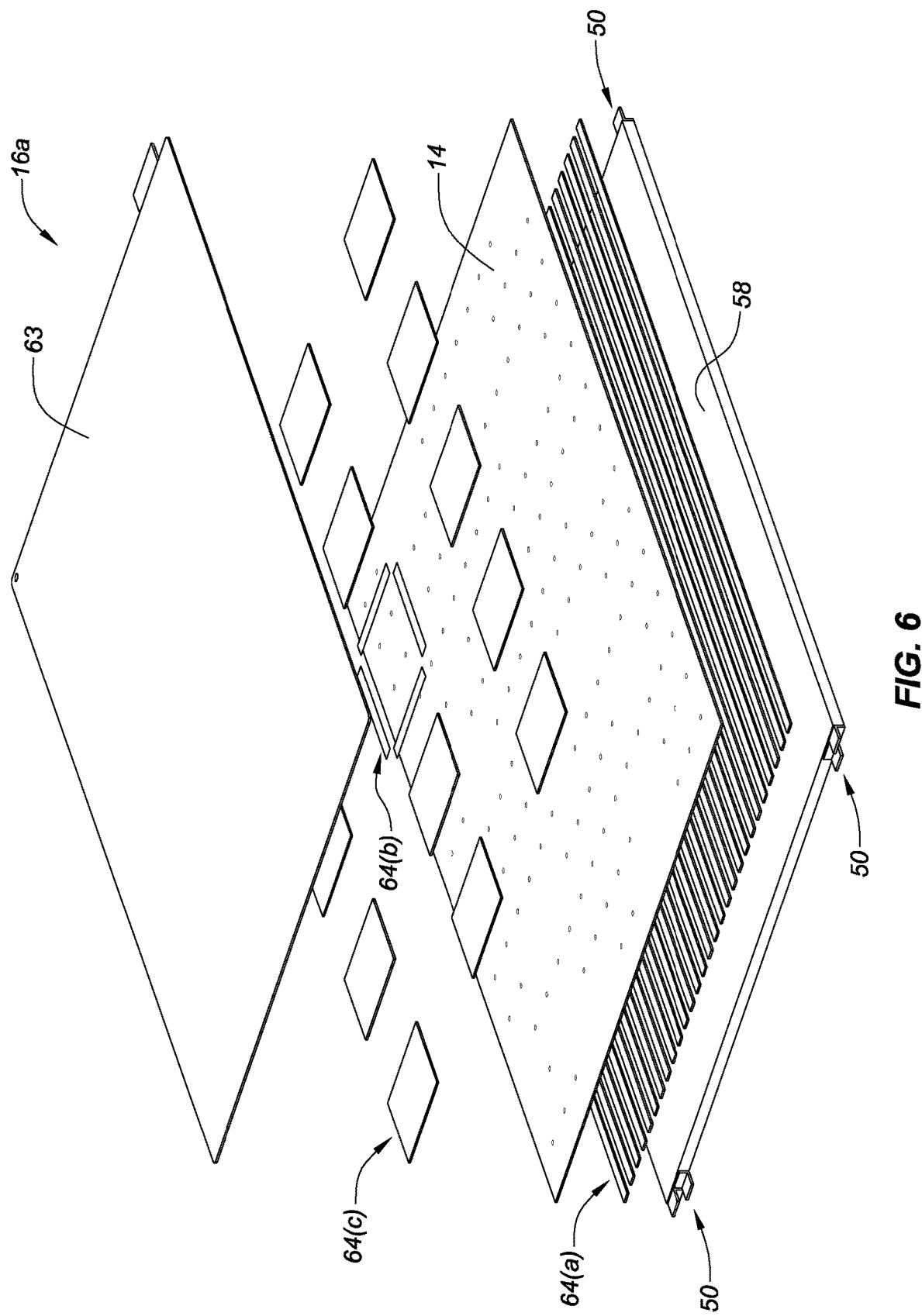
FIG. 6 is a first exploded view of elements comprising the internal portion of the registration plate.
Figure 7:
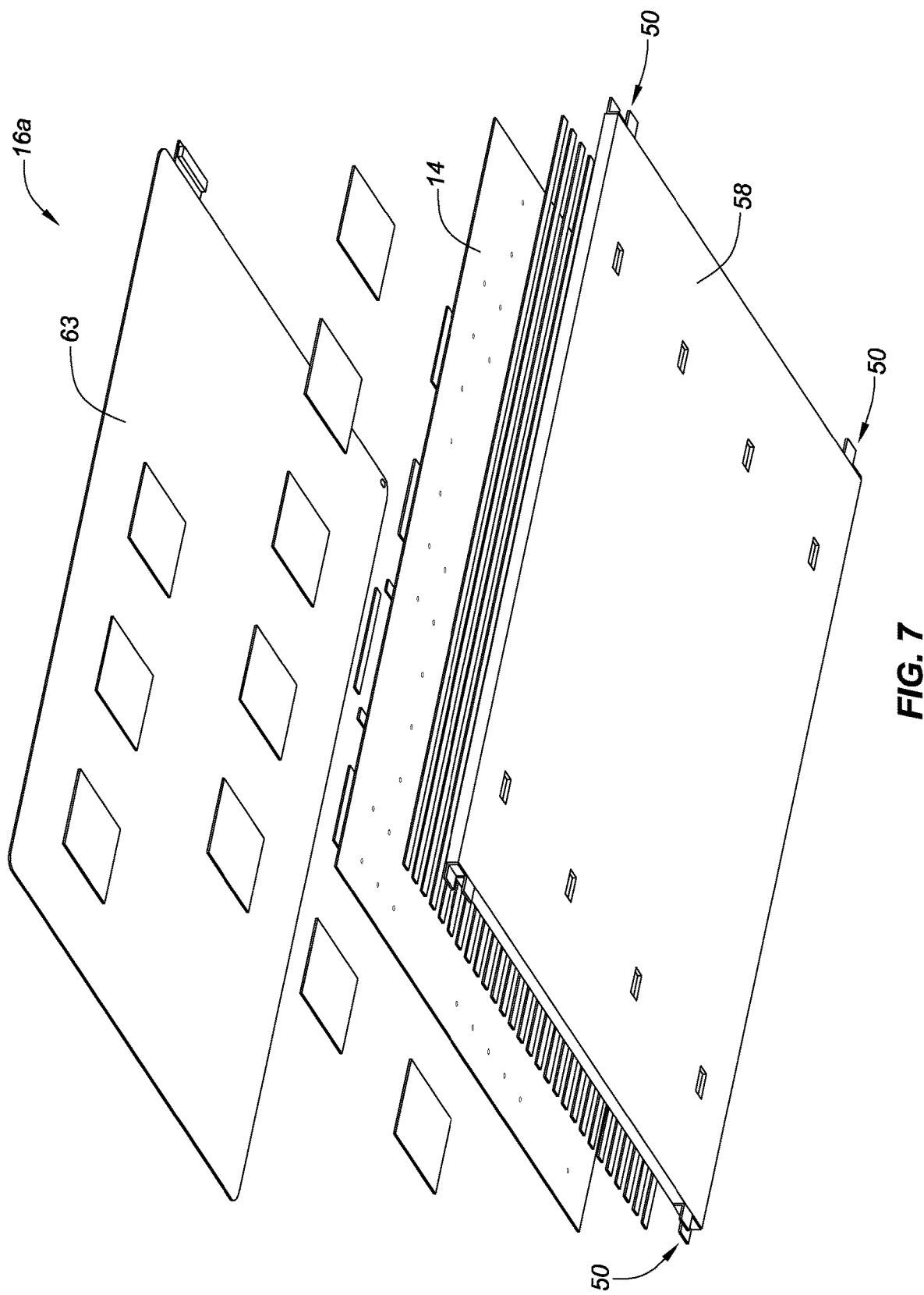
FIG. 7 is a second exploded view of elements comprising the internal portion of the registration plate.
Figure 8:
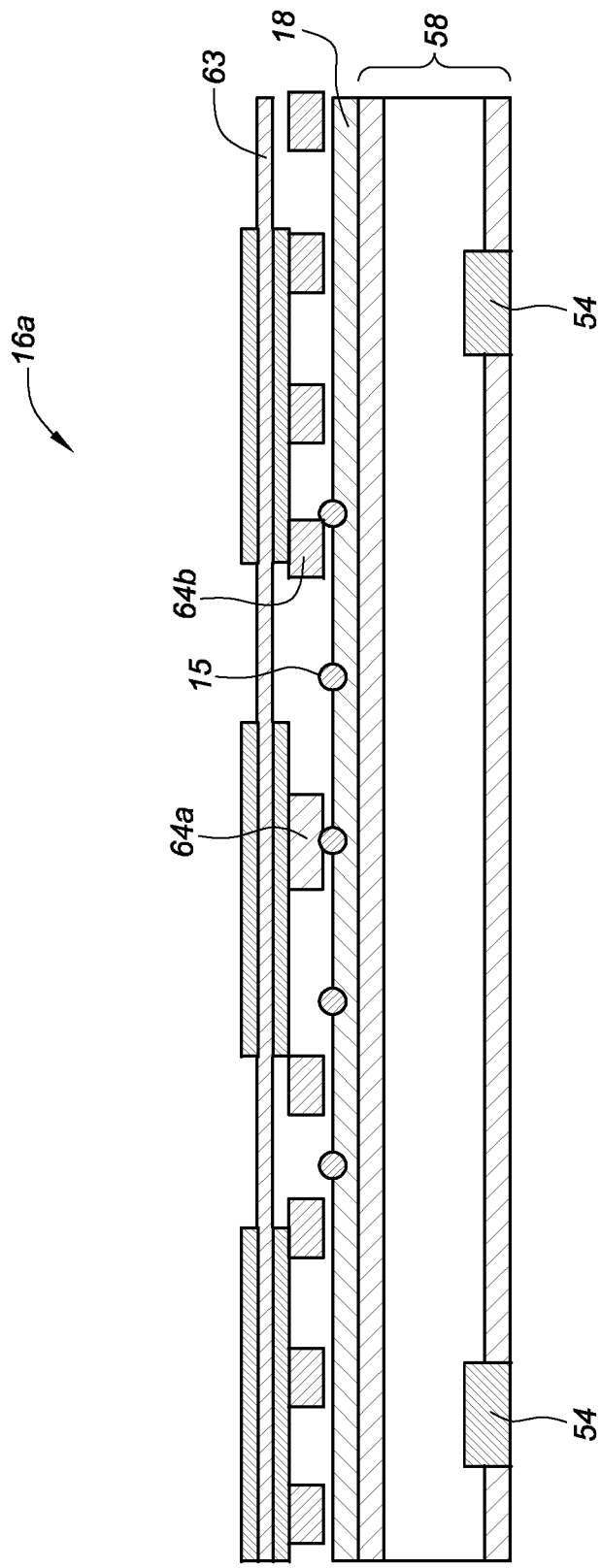
FIG. 8 is a side view of elements comprising the internal portion of the registration plate.

A further embodiment of the thin, flat PCB-type coil assembly 63 included within the internal portion of OMRP plate 16a is shown in FIGS. 6-8, which are exploded top, exploded bottom, and side views, respectively. In this embodiment, the fiducial layer 14 containing fiducial markers 15 is shown separated from the rigid internal structure 58. A first adhesive 64(a) can be used to bond the fiducial layer 14 to the rigid internal structure 58. A second adhesive 64(b) can be used to bond the fiducial layer 14 to the flat coil assembly 63. Both the first adhesive 64(a) and the second adhesive 64(b) can comprise, for example, Araldite® 2011—A/B by Huntsman or Hysol® EA 9396 by Henkel. A third adhesive 64(c), such as PPG Aerospace #PR-2701 or Loctite Henkel SMP Adhesive #5590, for example, can also be used to bond the fiducial layer 14 to the flat coil assembly 63.

Reduced X-Ray Image Artifacts

Reduced impact on X-ray image quality can be achieved by using a homogeneous structure for the components visible in the X-ray field of view. Therefore, when the rigid internal structure 58 is comprised of layers of carbon fiber, for example, it is important that carbon fiber and the epoxy bonding between the layers have similar X-ray absorption. If possible, sharp edges between materials of different thicknesses can be replaced by smoother edges. In addition, X-ray aging may cause changes in the X-ray absorption rate of some materials, affecting the homogeneity of the rigid internal structure 58 and resulting in the creation of image artifacts. To prevent this, materials with low X-ray aging properties (e.g., carbon fibers) can be used to ensure homogeneity over time.

Reduced Impact on X-Ray System Movement Envelope

The table-mounted sub-assembly cab be configured to change the movement envelope of the X-ray system 10 as little as possible. For example, the OMRP plate 16 can be configured and positioned so as to avoid mechanical collision with the X-ray imaging system 10 or interference with the X-ray image. Using a thin tabletop box placed under the patient mattress is an optimal solution relative to an under-the-table fixture (which can limit movement of the X-ray emitter 26).

Minimal Impact on Patient Comfort

Since the patient lies on a mattress covering the table-mounted OMRP plate 16 and the table 20, the OMRP plate 16 may be as thin as possible and can have smooth edges. In an embodiment, the OMRP plate 16 can be about 500 mm long and about 500 mm wide. Additionally, the height (or thickness) of the OMRP plate 16 can be about 15 mm. In an example, the height of the OMRP plate 16 is approximately 14.9 mm.

In addition to the above considerations, and as discussed further below, the present magnetic tracking system design also considered the following: robustness to external forces, robustness to environmental conditions (humidity, pressure, and temperature), robustness to magnetic field metal distortion effect (the system's sub-components should not distort its own magnetic field), and robustness to X-ray exposure over time.

Robustness to External Factors

Figure 9:
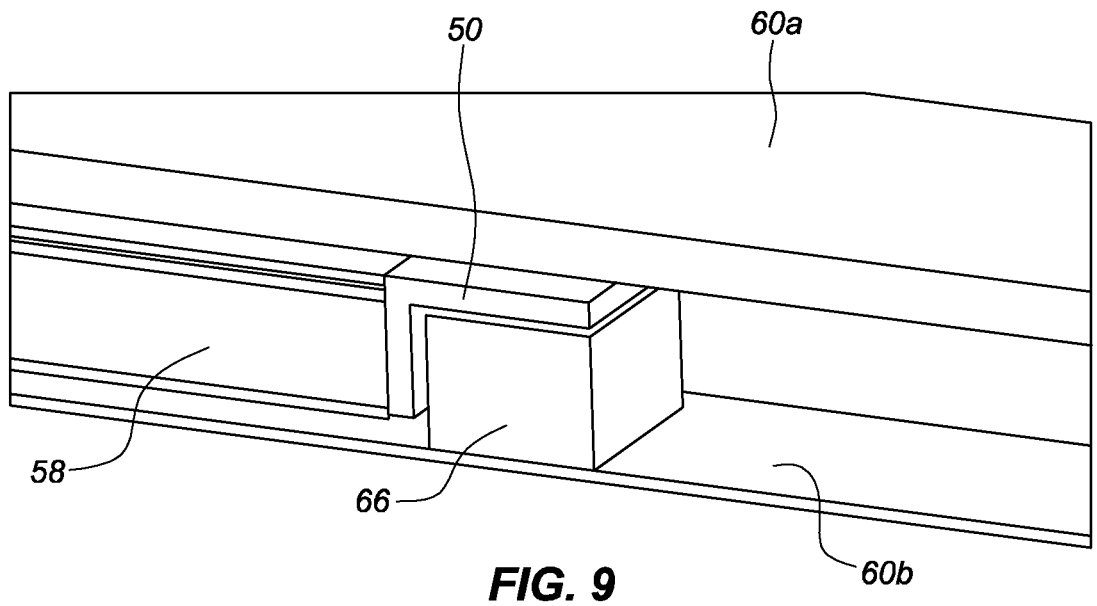
FIG. 9 is an enlarged side view of an internal portion of the registration plate.

The OMRP plate 16 is exposed, during clinical procedures, to forces generated by the patient's weight, table top bending, and mechanical collision. Since the functionality of the table-mounted OMRP plate 16 is very sensitive to geometry modifications, the internal rigid structure 58 may be protected from deformations as a result of such external factors. To eliminate the impact of external forces, the mechanical design the internal rigid structure 58 is protected by a floating mechanism within the external enclosure, as can be seen in FIG. 4. The floating mechanism is implemented using one or more silicon springs 66 placed at or near the corners of the rigid internal structure 58, as can be seen in FIG. 9. The floating mechanism and external enclosure may be components of the protective housing 60 discussed above.

Robustness to Environmental Conditions

To protect the internal components of the rigid internal structure 58 from humidity, the sub-assembly protective enclosure can be sealed, using silicon gaskets (e.g., silicon gasket 61 shown in FIG. 4) for example, to close gaps between detachable parts. To avoid damage to the OMRP plate 16 as a result of inner/outer pressure differences during storage and transportation, a pressure equalization means may be employed. This can be achieved using two unidirectional pressure valves, for example. The residual humidity resulting from air exchange during the pressure equalization process can be absorbed by including desiccant packages within the enclosure.

Ensuring consistent performance throughout an operating temperature span of the OMRP plate 16 may require continuous temperature monitoring and temperature dissipation mechanisms. Temperature monitoring can be achieved by employing an array of thermocouple sensors or, alternatively, by measuring a change in the electrical resistance of the field generator coils. To decrease temperature variance, a closed-loop cooling system can be implemented. An example of such a closed loop cooling system includes piezoelectric fans (not shown) for internal air circulation combined with heat transfer mechanism to the patient tabletop.

In some embodiments, it may be beneficial to monitor and compensate for temperature changes in magnetic coils of the OMRP plate because thermal expansion of the coils can lead to image degradation and difficulty detecting fiducial markers. As noted above, temperature monitoring of the OMRP plate 16—and specifically of the magnetic field transmitters 46 and/or the flat coil assembly 63—can be achieved by measuring the change in the electrical resistance of the magnetic coils. Doing so avoids potential excess X-ray attenuation and/or interference with X-ray images resulting from the use of thermocouples or thermometers that are not X-ray translucent/transparent.

Based on the linear linkage between temperature and electrical resistance, the following equation can be used:

$$R = R_{Ref}[1 + \alpha(T - T_{Ref})] \quad \text{(Eq1)}$$

where, $R_{Ref}$—Measured resistance @ $T_{Ref}$ $\alpha$—Material coefficient (e.g., 0.00404 for Copper or 0.0043 for Aluminum).

$R_{Ref}$ can be measured in a well-known and calibrated environment, where $T_{Ref}$ is well known and accurate. From Eq 1, T (temperature) can be found by measuring R (resistance) as follows:

$$T = \left(\frac{R}{R_{Ref}} - 1\right)\frac{1}{\alpha} + T_{Ref}. \quad \text{(Eq 2)}$$

For a DC-based circuit, R can be calculated as follows:

$$R = \frac{V_{dc}}{I_{dc}}.$$

For an AC-based circuit, with AC coupling, R can be calculated as follows:

$$\frac{v_{ac}}{i_{ac}} = \vec{z}$$

$$z = z_c + z_l = \frac{1}{jwc} + jwl + R_{*(w=2\pi f)}$$

$$R = \frac{jwcz - 1 + w^2 lc}{jwc} \quad \text{(Eq 3)}$$

where $v_{ac}$ is voltage in the AC-based circuit, $i_{ac}$ is current in the AC-based circuit, c is capacitance, l is inductance, z is equivalent impedance, $z_c$ is capacitive equivalent impedance, $z_l$ is inductive equivalent impedance, f is frequency (Hertz), w is frequency (radians/second), and j is the square root of negative one. For either DC-based or AC-based circuits, once R is calculated it can be used in Eq 2 above to calculate the T (temperature) of the coils.

Robustness to Metal Distortion

Figure 10:
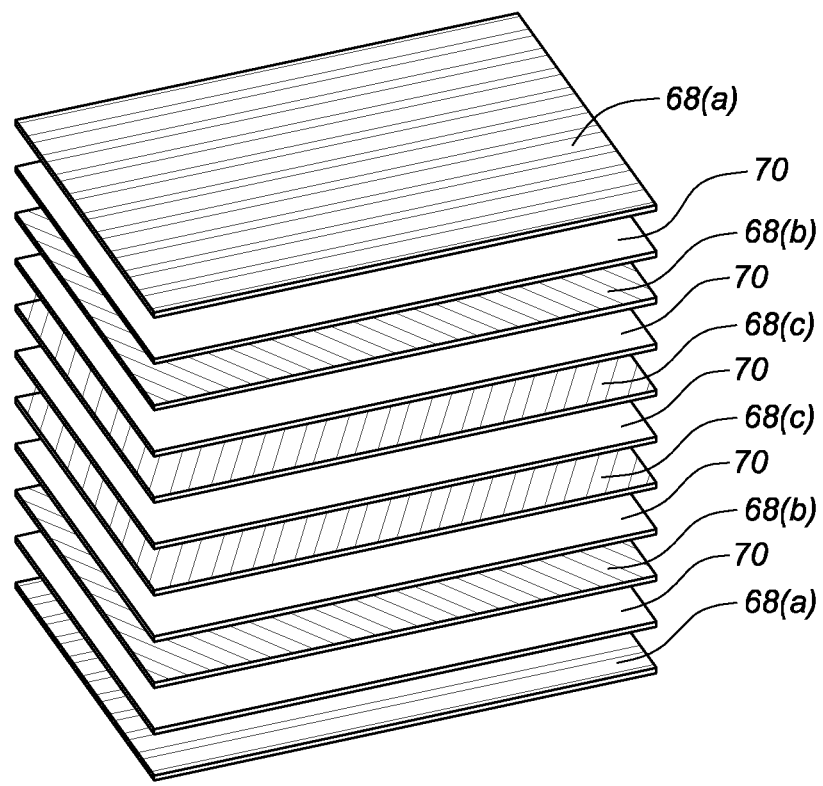
FIG. 10 is an isometric view of an example of a stack of unidirectional carbon fiber layers with isolation between the different layers.

Eddy currents are generated in a conductive material in the presence of an electro-magnetic field. The eddy currents create a parasitic electro-magnetic field which degrades the magnetic tracking performance. Thus, the eddy currents should be minimized. As explained above, a preferred material for the rigid internal structure 58 of the OMRP plate 16 is carbon fiber. Twill-woven carbon fiber plates are conductive and generate eddy currents when placed in a dynamic magnetic field and, therefore, are not suited for the magnetic environment. A preferred composition for the magnetic application is a stack of unidirectional carbon fiber layers with isolation between the different layers, an example of which is shown in FIG. 10. In this embodiment, carbon fiber layers 68(a) comprise carbon fibers arranged horizontally, carbon fiber layers 68(b) comprise carbon fibers arranged in a first diagonal direction, and carbon fiber layers 68(c) comprise carbon fibers arranged in a second diagonal direction. An isolation layer 70 lies in between each carbon fiber layer. This arrangement helps to minimize eddy currents.

In addition, to further eliminate impact on the magnetic field, metal components should be avoided, if possible, for the entire apparatus and enclosure components. For example, the springs 66 designed to suspend the rigid structure can be made out of non-conductive silicon.

Robustness to X-Ray Exposure Over Time

The table-mounted sub-assembly is continuously exposed to direct X-ray radiation during clinical procedures. X-ray exposure may change the material properties over time, resulting in degraded mechanical strength (impacting robustness) and changes in X-ray absorbance (creating image artifacts). Therefore, selection materials with slow X-ray aging properties—such as carbon, polymethacrylimide foam, and silicon materials, for example—is preferred in some embodiments.

Although at least one embodiment of a registration fixture and its associated sub-assembly components has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments,"

"in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A registration fixture configured for use with a medical imaging system, the registration fixture comprising:
   a rigid internal structure comprising a plurality of fiducial markers arranged in a predefined pattern, the rigid internal structure comprising four corners;
   a housing configured to surround the rigid internal structure; and
   a plurality of silicon springs configured to allow the rigid internal structure to float within the housing, wherein each of the four corners is supported by one of the plurality of silicon springs;
   wherein the registration fixture is configured to be mounted on a patient table.

2. The registration fixture of claim 1, wherein the plurality of silicon springs is configured to protect the rigid internal structure from deformations as a result of external factors.

3. The registration fixture of claim 1, further comprising one or more attachment components configured to releasably secure the registration fixture to at least one magnetic field transmitter.

4. The registration fixture of claim 3, wherein a transmitter clamp attached to the magnetic field transmitter is configured to releasably couple to the one or more attachment components of the registration fixture.

5. The registration fixture of claim 1, the housing defining a volume between a top housing and a bottom housing, rigid internal structure positioned within a first area of the volume, the registration fixture further comprising at least one magnetic sensor positioned within a second area of the volume, the second area positioned between the first area and a side of the housing so as to limit potential interference with a field of view of the medical imaging system.

6. The registration fixture of claim 1, wherein the rigid internal structure further includes one or more layers of an assembly of flat coils configured to transmit magnetic fields.

7. The registration fixture of claim 1, wherein at least one of the rigid internal structure and the housing comprises a stack of unidirectional carbon fiber layers.

8. The registration fixture of claim 1, wherein the plurality of fiducial markers comprises at least one layer of radio-opaque ball or line elements.

9. The registration fixture of claim 1, further comprising at least one of:
   a temperature monitoring mechanism comprising a mechanism of monitoring an electrical resistance of a magnetic field transmitter or coil within the registration fixture; and
   a temperature dissipation mechanism.

10. The registration fixture of claim 1, wherein a 3D coordinate system of the fixture is registerable with a 2D image produced by the medical imaging system.

11. A registration fixture configured for use with a medical imaging system, the registration fixture comprising:
    a rigid internal structure comprising a plurality of fiducial markers arranged in a predefined pattern; and
    a housing configured to surround the rigid internal structure;
    wherein the registration fixture is configured to be mounted on a patient table; and
    wherein the rigid internal structure comprises a stack of unidirectional carbon fiber layers and isolation between each pair of unidirectional carbon fiber layers.

12. The registration fixture of claim 11, wherein the stack of unidirectional carbon fiber layers comprises at least one layer of carbon fibers arranged unidirectionally in a first direction and at least one layer of carbon fiber layers arranged unidirectionally in a second direction.

13. The registration fixture of claim 11, wherein the housing comprises a stack of unidirectional carbon fiber layers.

14. The registration fixture of claim 11, further comprising a floating mechanism configured to allow the rigid internal structure to float within the housing; wherein the floating mechanism comprises at least one silicon spring located at or near at least one corner of the rigid internal structure.

15. The registration fixture of claim 11, the housing comprising defining a volume between a top housing and a bottom housing, rigid internal structure positioned within a first area of the volume and further comprising at least one magnetic field transmitter positioned within a second area of the volume, the second area to the side of the first area.

16. The registration fixture of claim 11, wherein the rigid internal structure further includes an assembly of flat coils configured to transmit magnetic fields.

17. The registration fixture of claim 11, further comprising at least one of:
    a temperature monitoring mechanism comprising a mechanism of monitoring an electrical resistance of a magnetic field transmitter or coil within the registration fixture; and
    a temperature dissipation mechanism.

18. The registration fixture of claim 11, wherein a 3D coordinate system of the fixture is registerable with a 2D image produced by the medical imaging system.

19. The registration fixture of claim 11, wherein the registration fixture is an optical-magnetic registration fixture configured for use with a fluoroscopic imaging system.

20. An optical-magnetic registration fixture configured for use with a fluoroscopic imaging system during a clinical procedure, the registration optical-magnetic fixture comprising:
- a housing comprising a top housing and a bottom housing, the housing defining a volume between the top housing and the bottom housing, the volume comprising a first area and a second area, wherein the second area is positioned adjacent to at least one side of the first area;
- a rigid internal structure positioned in the first area of the volume;
- a fiducial layer coupled to the rigid internal structure, the fiducial layer comprising a plurality of fiducial markers arranged in a predefined pattern and configured to be visible in a fluoroscopic image; and
- one or more magnetic sensors positioned only in the second area of the volume.

21. The optical-magnetic registration fixture of claim 20, further comprising a layer of flat magnetic transmitter coils coupled to the fiducial layer.

22. The optical-magnetic registration fixture of claim 20, wherein the rigid internal structure is suspended above the bottom housing by one or more silicon springs.

* * * * *